United States Patent
Corcoran

(10) Patent No.: US 7,338,282 B2
(45) Date of Patent: Mar. 4, 2008

(54) SINGLE PATIENT PACKAGE FOR DENTAL APPLIANCES AND METHODS OF USING

(75) Inventor: Kevin Sean Corcoran, Corona, CA (US)

(73) Assignee: Ormco Corporation, Orange, CA (US)

( * ) Notice: Subject to any disclaimer, the term of this patent is extended or adjusted under 35 U.S.C. 154(b) by 518 days.

(21) Appl. No.: 10/940,318

(22) Filed: Sep. 14, 2004

(65) Prior Publication Data

US 2006/0054515 A1 Mar. 16, 2006

(51) Int. Cl.
*A61C 3/00* (2006.01)
*A61C 13/38* (2006.01)
*A61C 19/00* (2006.01)
*A61B 19/02* (2006.01)

(52) U.S. Cl. .................. 433/2; 206/63.5; 206/369; 433/26; 433/79

(58) Field of Classification Search ............... 206/63.5, 206/369, 459.5, 562–564, 83; 433/2, 8–9, 433/24–25, 77, 26, 79
See application file for complete search history.

(56) References Cited

U.S. PATENT DOCUMENTS

| | | | |
|---|---|---|---|
| 4,952,204 A | | 8/1990 | Korteweg |
| 4,978,007 A | * | 12/1990 | Jacobs et al. ............... 206/368 |
| 5,199,567 A | * | 4/1993 | Discko, Jr. ................. 206/369 |
| 5,221,202 A | * | 6/1993 | James ......................... 433/9 |
| 5,289,919 A | * | 3/1994 | Fischer ....................... 206/369 |
| 5,348,154 A | * | 9/1994 | Jacobs et al. ............... 206/369 |
| 5,350,059 A | | 9/1994 | Chester et al. |
| 5,354,199 A | | 10/1994 | Jacobs et al. |
| 5,636,736 A | | 6/1997 | Jacobs et al. |
| 5,660,273 A | | 8/1997 | Discko, Jr. |
| 5,692,896 A | | 12/1997 | Pospisil et al. |
| 5,697,780 A | * | 12/1997 | Tuneberg et al. ............... 433/9 |
| 5,756,174 A | | 5/1998 | Tuneberg |
| 5,759,028 A | | 6/1998 | Bozman |
| 5,827,058 A | | 10/1998 | Kelly et al. |
| 6,089,861 A | | 7/2000 | Kelly et al. |
| 6,213,767 B1 | | 4/2001 | Dixon et al. |
| 6,415,916 B1 | * | 7/2002 | Rini ........................... 433/26 |
| 6,482,003 B2 | | 11/2002 | Dixon et al. |
| 6,834,761 B1 | * | 12/2004 | Kesling ........................ 206/63.5 |
| 2005/0178685 A1 | * | 8/2005 | Corcoran et al. ........... 206/369 |
| 2006/0175209 A1 | * | 8/2006 | Sabilla et al. ............... 206/63.5 |

* cited by examiner

*Primary Examiner*—Bryon P Gehman
(74) *Attorney, Agent, or Firm*—Wood, Herron & Evans, L.L.P.

(57) ABSTRACT

Packages for dispensing dental appliances of the type used in corrective orthodontic treatments, methods of using such packages, and methods of manufacturing such packages. The package generally includes a holder and drawers containing the dental appliances that are removable from the package. The characteristics of the dental appliances positioned in each individual drawer are appropriate for application to different quadrants of the patient's teeth. The drawers of the package may be color coded with regions on a setup card so that the dental appliances, while remaining positioned in the drawers, may be organized among the regions according to the intended quadrants for bracket application. Other color coding schemes are possible involving the drawers, the brackets held by the drawers, the setup card, and the brackets themselves.

31 Claims, 6 Drawing Sheets

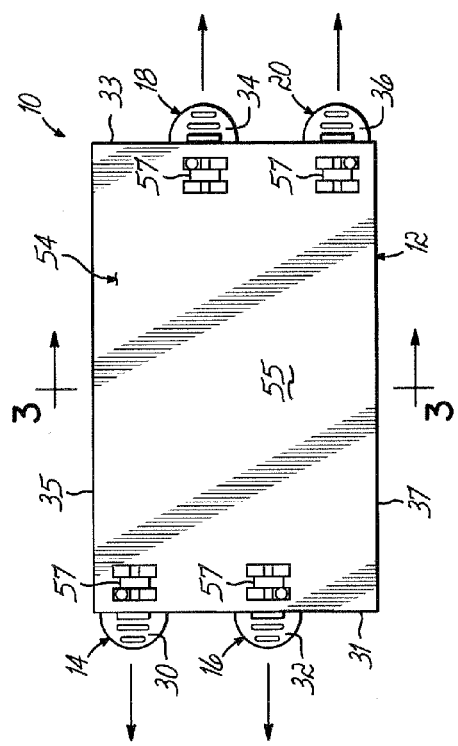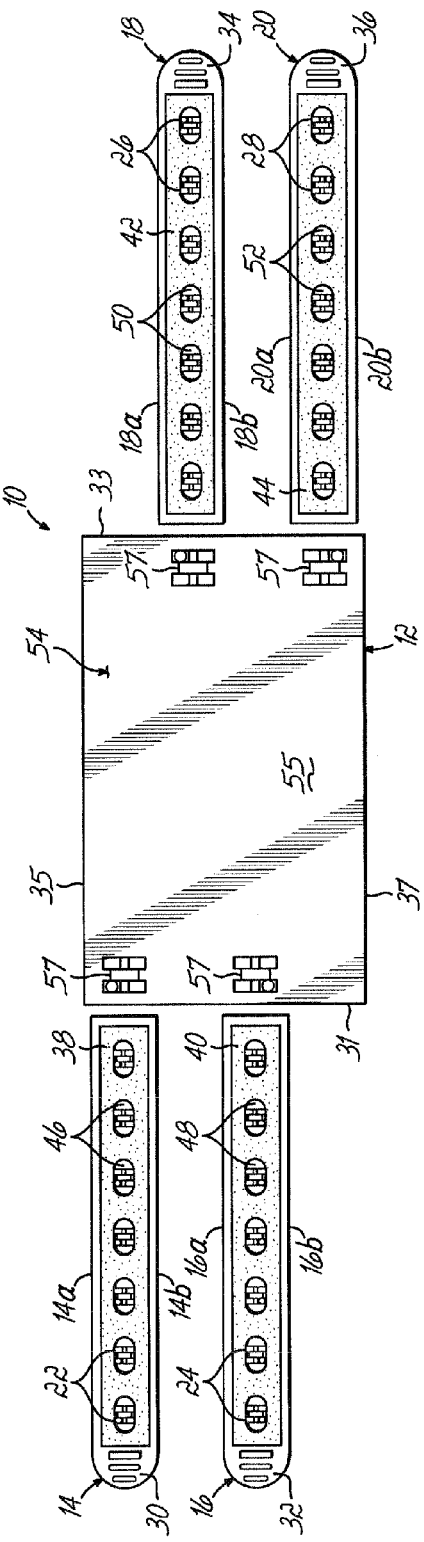
FIG. 1
FIG. 2

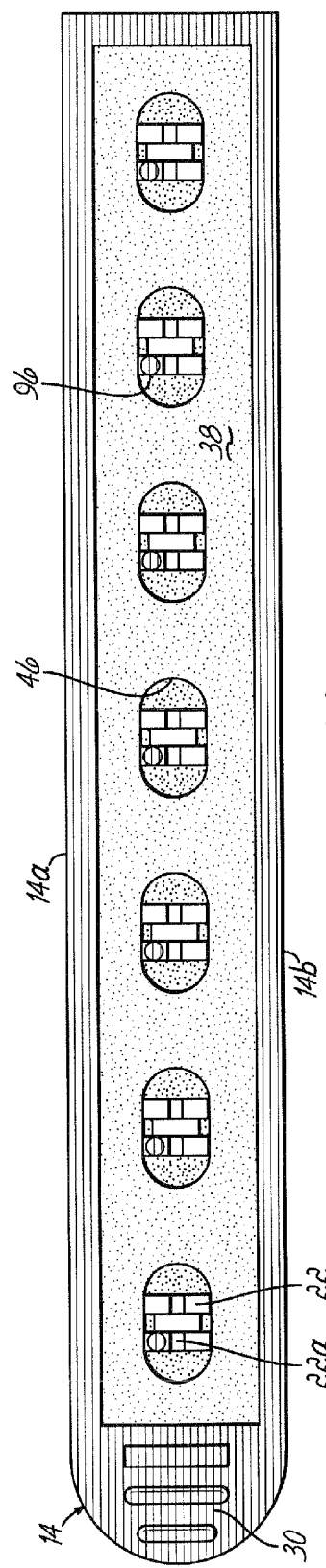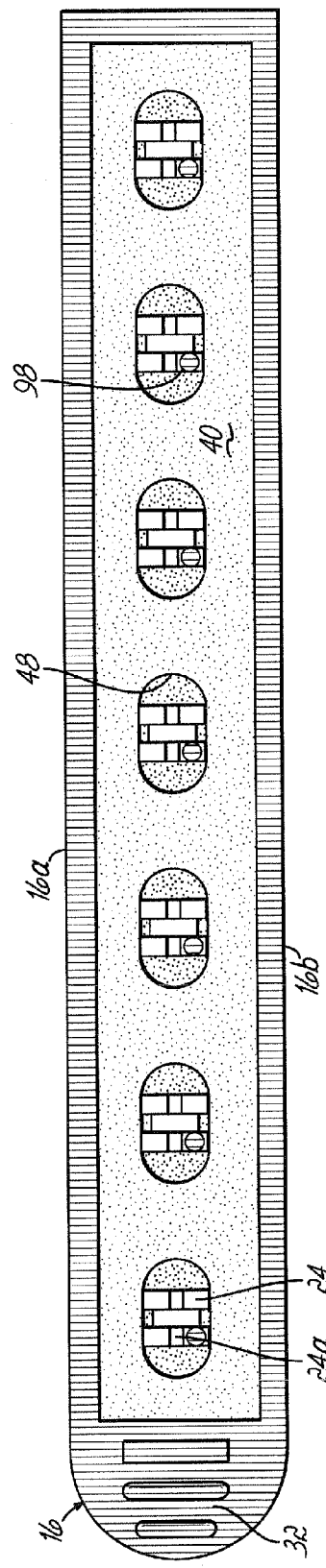

SINGLE PATIENT PACKAGE FOR DENTAL APPLIANCES AND METHODS OF USING

FIELD OF THE INVENTION

The invention relates generally to dental packaging and, more particularly, to packages for dispensing dental appliances of the type used in orthodontic treatment and methods of using and manufacturing such packages.

BACKGROUND OF THE INVENTION

In corrective orthodontic treatments, dental appliances in the form of brackets are used to move malpositioned teeth to orthodontically correct positions for improving a patient's occlusion. Conventional orthodontic treatments apply brackets to the patient's teeth and thread an archwire through a slot defined in each bracket. The archwire applies corrective forces to the brackets directed to coerce the patient's teeth to move to orthodontically correct positions.

During set up for an orthodontic treatment, the individual brackets from among a group of dental appliances are placed at labeled tooth positions on a setup card. One significant disadvantage of such set up processes is that placing the individual brackets onto the setup card at the proper tooth positions and with a correct orientation is time consuming for the clinician or the clinician's assistant. Another disadvantage is that the individual brackets may be easily positioned at incorrect tooth positions on the setup card. Yet another disadvantage is the potential for bracket contamination, such as the transfer of dirt and oils to the bracket surfaces, during handling by the clinician.

If the brackets are supplied in a single patient package, the clinician may avoid transferring the brackets to the setup card by working directly from the package. In practice, most single patient bracket packages are not constructed to work directly with a setup card, which forces the clinician to work directly from the package. The brackets are loose inside conventional single patient bracket packages. The clinician or clinician's assistant must identify a quadrant and a specific tooth in the quadrant for each bracket removed from such packages and then orient the bracket removal. This sequence of events slows bracket application and introduces uncertainty in the identity and orientation of the brackets handed from the assistant to the clinician. Any unused brackets must be either stored loose with a risk of loss or stored in the bulky original package.

Therefore, a single patient package for orthodontic brackets is needed that overcomes these deficiencies of conventional single patient packages.

SUMMARY OF THE INVENTION

The invention overcomes the foregoing and other shortcomings and drawbacks of conventional single patient bracket packaging, as described above. In accordance with one embodiment of the invention, a package for use in orthodontic treatment comprises a first drawer containing a first plurality of dental appliances intended for use on a first quadrant of a patient's teeth, a second drawer containing a second plurality of dental appliances intended for use on a second quadrant of the patient's teeth, and a holder supporting the first and second drawers. The first and second drawers can be separately opened by movement relative to the holder to access the corresponding dental appliances for removal.

In another embodiment of the invention, a package for use in orthodontic treatment of a patient's teeth comprises a holder including a cover and a flange structure defining a plurality of channels. The package further comprises a plurality of drawers each received in a respective one of the channels. Each of the drawers has a plurality of recesses in which a dental appliance is received. Each of the drawers is oriented such that the recesses open toward the cover. Each of the drawers is movable in its channel relative to the flange structure from a covered position beneath the cover to an opened position suitable for accessing the recesses.

In another embodiment of the invention, a package for use in orthodontic treatment of a quadrant of a patient's teeth comprises a drawer having a plurality of recesses and a longitudinal axis. The package further includes a plurality of dental appliances each configured for use on a tooth in the quadrant of the patient's teeth. Each of the dental appliances is positioned in a corresponding one of the recesses and has a feature that is oriented with a common angular orientation relative to the longitudinal axis of the drawer.

In yet another embodiment of the invention, a kit for use in orthodontic treatment includes a holder with a plurality of removable drawers, a plurality of dental appliances received in the drawers, and a setup card having a plurality of regions defining placement locations for the drawers. Each of the regions on the setup card and a corresponding one of the drawers have a different color representing a color code and identifying an intended location of use for the dental appliances in each drawer on a different quadrant of the patient's teeth.

In yet another embodiment of the invention, a method is provided for using a package with multiple drawers each holding dental appliances intended for use in a different quadrant of a patient's teeth. The method includes opening a first drawer to access the dental appliances intended for use on a first quadrant of the patient's teeth, removing the dental appliances from the first drawer, and mounting the dental appliances removed from the first drawer to the first quadrant of the patient's teeth. The opened first drawer may be separated or removed from the package and placed on a setup card before the dental appliances are removed and mounted to the patient's teeth.

In yet another embodiment of the invention, a method for bonding dental appliances to a patient's teeth includes selecting from a package a first drawer containing dental appliances intended for use on a first quadrant of the patient's teeth and placing the first drawer on a setup card having adhesive thereon for holding the first drawer in place. The method further includes selecting dental appliances from the first drawer and then mounting the dental appliances to the patient's teeth in the first quadrant.

In yet another embodiment of the invention, a method is provided for using a package holding multiple drawers each of a different color in which each of the drawers contains dental appliances intended for use in a different quadrant of a patient's teeth. The method comprises removing from the package a first drawer having a first color and containing dental appliances for use on a first quadrant of the patient's teeth, positioning the first drawer on a first region of a setup card having the first color, and removing the dental appliances from the first drawer. The method further includes mounting the dental appliances removed from the first drawer on the patient's teeth in the first quadrant.

In yet another embodiment of the invention, a method is provided for using a package holding multiple drawers each containing dental appliances with an indicia of different color intended for use in a different quadrant of a patient's teeth. The method includes removing from the package a first drawer containing dental appliances having an indicia with a first color and configured for use on a first quadrant of the patient's teeth, positioning the first drawer on a first region of a setup card having the first color, and removing the dental appliances from the first drawer. The method further includes mounting the dental appliances on the patient's teeth in the first quadrant.

In yet another embodiment of the invention, a method of manufacturing a package for use in orthodontic treatment of a patient's teeth includes defining a plurality of recesses in a drawer. The method further includes orienting a feature on each of a plurality of dental appliances with a common angular orientation relative to a longitudinal axis of the drawer.

The above and other objects and advantages of the invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 is a top view of a single patient bracket package in accordance with the invention;

FIG. 2 is an exploded top view of the single patient bracket package of FIG. 1;

FIGS. 4A-D are top views of the individual drawers of the single patient bracket package of FIG. 1;

DETAILED DESCRIPTION

The invention is directed to a single patient bracket package used to supply a set of appliances, which may be orthodontic brackets, to a clinician for application to perform a corrective orthodontic treatment. Although the invention will be described next in connection with certain embodiments, the invention is not limited to practice in any one specific type of appliance. It is contemplated that the package of the invention may be used with a variety of appliances, including but not limited to conventional orthodontic brackets and self-ligating orthodontic brackets. Alternatively, some or all of the dental appliances held by the package may be orthodontic buccal tubes or other types of dental devices adapted to be bonded to a tooth surface or other structure inside a patient's mouth.

Figure 3:
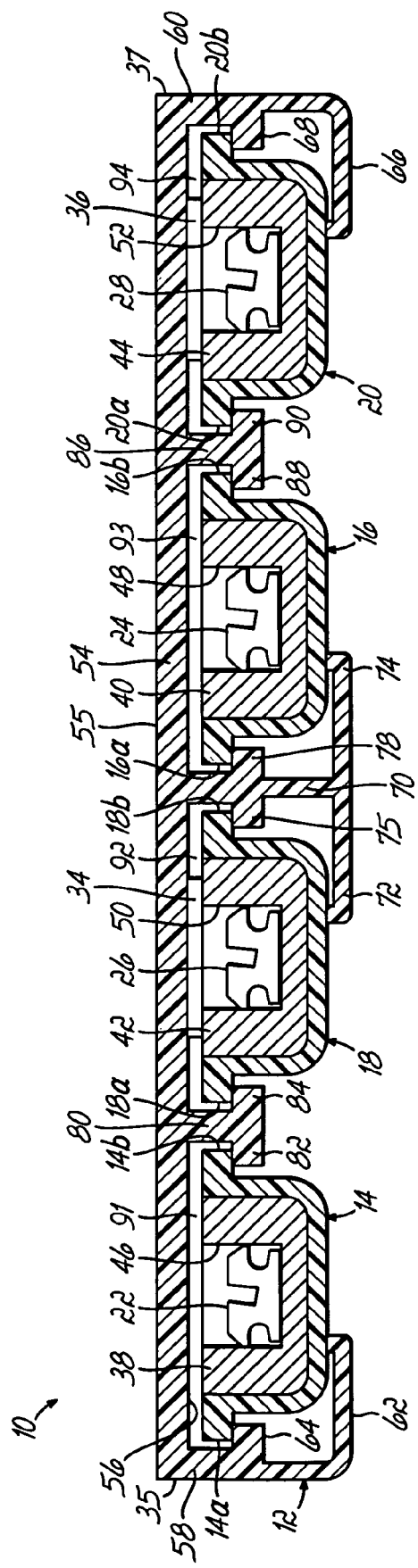
FIG. 3 is a cross-sectional view taken generally along line 3-3 in FIG. 1.
Figure 4C:
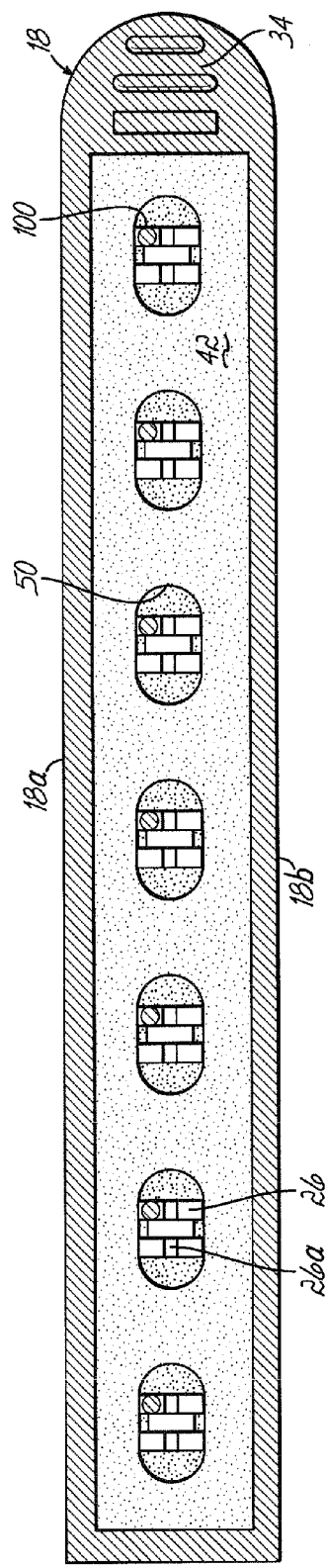
Figure 4D:
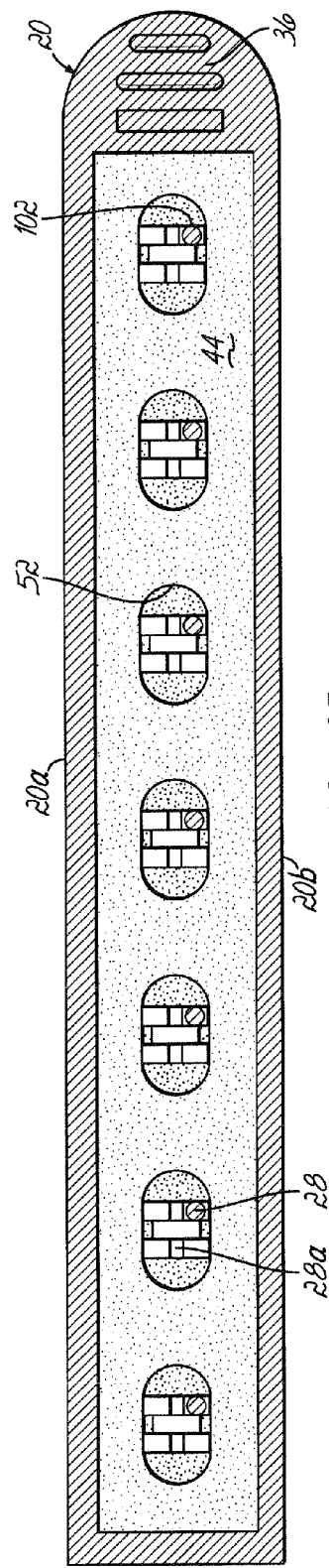

With reference to FIGS. 1-3, a single patient bracket package, generally indicated by reference numeral 10, includes a holder 12 and a plurality of slide drawers 14, 16, 18, 20 coupled with the holder 12. The holder 12 and slide drawers 14, 16, 18, 20 are preferably molded from a polymer resin suitable for dental applications. The holder 12 is generally geometrically shaped as a three-dimensional parallelopiped having substantially rectangular faces to facilitate shipping, storage and handling, and yet provides a relatively compact protective enclosure for the slide drawers 14, 16, 18, 20. The geometrical shape permits multiple packages 10 to be stacked for storage and packed in a compact manner inside a container for shipment from a supplier to an end user, such as a clinician. To that end, the geometrical shape of holder 12 permits multiple holders 12 to be disposed closely adjacent one another along their sidewalls to, for example, form an extensive, substantially continuous layer of holders 12.

Slide drawers 14, 16, 18, 20 are secured in a closed position in a location inside the holder 12 in which dental appliances, such as brackets 22, 24, 26, 28, respectively, are inaccessible from the exterior of the package 10. Slide drawers 14, 16, 18, 20 may be of substantially identical length, width and depth, although the construction of drawers 14, 16, 18, 20 is not so limited. Each of the slide drawers 14, 16 18, 20 is movable in a direction generally indicated by the single headed arrows on FIG. 1 to an opened position in which the brackets 22, 24, 26, 28, respectively, are accessible from the exterior of the package 10 and removable from package 10. The slide drawers 14, 16, 18, 20 may be separated from the holder 12 after opening or, alternatively, may be supported by the holder 12 in the opened position with the brackets 22, 24, 26, 28 in accessible locations for removal by a clinician or clinician's assistant.

Slide drawers 14 and 16 include a release tab 30 and 32, respectively, exposed along one end 31 of the holder 12 when the slide drawers 14 and 16 are in the closed position. Similarly, slide drawers 18 and 20 include a release tab 34 and 36, respectively, that is exposed along an opposite end 33 of the holder 12 when the slide drawers 18 and 20 are in the closed position. The release tabs 30, 32, 34, 36 provide convenient handles for grasping and moving the respective slide drawers 14, 16, 18, 20. Specifically, slide drawers 14, 16 may be individually moved from the closed position to the opened position by grasping the respective release tab 30, 32 and supplying a manual force in a lateral direction as indicated by the single-headed arrows pointing away from end 31 in FIG. 1. In the closed position, the drawers 14, 16, 18, 20 are inaccessible from opposed top and bottom sides 35, 37 of the holder 12. Each of the slide drawers 18, 20 may be individually moved from the closed position to the opened position by grasping the respective release tab 34, 36 and supplying a manual force in a lateral direction as indicated by the single-headed arrows pointing away from end 33 in FIG. 1. The release tabs 30, 32, 34, 36 may include raised ribs or other structure for grasping assistance or may optionally include identifiers, such as an embossed quadrant indicia.

With continued reference to FIGS. 1-3, located inside each of the slide drawers 14, 16, 18, 20 is an insert 38, 40, 42, 44, respectively, with exterior dimensions that conform to the geometrical shape of the recessed drawer interior. Defined in each of the inserts 38, 40, 42, 44 is a plurality of wells or recesses 46, 48, 50, 52, respectively, each of which is adapted to separately contain a corresponding one of the brackets 22, 24, 26, 28 for each tooth involved in the corrective orthodontic treatment. The inserts 38, 40, 42, 44 are preferably made of a flexible material that can readily deform to allow spreading movement for inserting the brackets 22, 24, 26, 28 into the corresponding recesses 46, 48, 50, 52 and yet have sufficient resilience and rigidity to securely hold the inserted bracket 22, 24, 26, 28 with a friction fit so that the pre-defined bracket orientation is preserved when the slide drawers 14, 16, 18, 20 are positioned in the stored position in holder 12. Preferred materials for the inserts 38, 40, 42, 44 include, for example, any conventional resilient foam like urethane, that is die cut to define the rectangular profile to match the recess in each of the drawers 14, 16, 18, 20 and to define the smaller recesses 46, 48, 50, 52.

The recesses 46, 48, 50, 52 are dimensioned and shaped to cooperate with the flexibility of the material of inserts 38, 40, 42, 44 for inserting and, thereafter, securely holding the brackets 22, 24, 26, 28 until deliberately removed from the package 10. The recesses 46, 48, 50, 52 are preferably oval-shaped but may have other geometrical shapes, such as diamonds or rectangles, dimensioned to provide the requisite friction fit with the brackets 22, 24, 26, 28. Because the specific number of recesses 46, 48, 50, 52 is application dependent, a greater or fewer number than seven recesses is possible. The invention contemplates that each of the slide drawers 14, 16, 18, 20 and the corresponding one of the inserts 38, 40, 42, 44 may be formed as an integral, one-piece structure from a material, like urethane, foam or paperboard, having sufficient structural stiffness to function as a support for brackets 22, 24, 26, 28 and yet adequate resiliency to grip the brackets 22, 24, 26, 28 with a friction fit within recesses 46, 48, 50, 52.

The characteristics of the individual brackets 22, 24, 26, 28 in each slide drawer 14, 16, 18, 20 may be selected to correlate with different jaw positions and teeth inside the patient's mouth. The brackets 22, 24, 26, 28 are adapted to be adhesively bonded directly to the tooth surface and each has an exterior base surface contoured to match the contour of the corresponding tooth. The brackets 22, 24, 26, 28 may be made of metal or another suitable material, such as a ceramic or a polymer. The separate drawers 14, 16, 18, 20, in combination with the holder 12, are advantageous during manufacture because different drawers, each holding a bracket for a different tooth, can be assembled in a single kit for a particular patient in accordance with the clinician's prescription.

In one embodiment, slide drawer 14 may be occupied by a set of brackets 22 destined to be attached to teeth in the upper right quadrant, slide drawer 16 may be occupied by a set of brackets 24 destined to be attached to teeth in the upper left quadrant, slide drawer 18 may be occupied by a set of brackets 26 for attachment to teeth in the lower right quadrant, and slide drawer 20 may be occupied by a set of brackets 28 for attachment to teeth in the lower left quadrant. The brackets 22, 24, 26, 28 contained within each slide drawer 14, 16, 18, 20 may either be identical or different from one another. Preferably, the brackets 22, 24, 26, 28 in each respective slide drawer 14, 16, 18, 20 are systematically arranged in the recesses 46, 48, 50, 52 of the corresponding insert 38, 40, 42, 44 according to the prospective tooth position relative to the jaw centerline (i.e., central incisor, lateral incisor, cuspid, first bicuspid, second bicuspid, first molar, second molar). Specifically, brackets 22, 24, 26, 28 for the central incisor of each of the four quadrants may be systematically positioned in the recess 46, 48, 50, 52 of the corresponding slide drawer 14, 16, 18, 20 nearest to the corresponding release tab 30, 32, 34, 36. Similarly, brackets 22, 24, 26, 28 destined to be applied to the second molar in each of the four quadrants may be systematically positioned in the recess 46, 48, 50, 52 of the corresponding slide drawer 14, 16, 18, 20 most remote from the corresponding one of the release tabs 30, 32, 34, 36.

Each of the brackets 22, 24, 26, 28 is preferably positioned in the corresponding set of recesses 46, 48, 50, 52 with a consistent three-dimensional orientation of an identifiable bracket feature. As a result, when the holder 10 is received by the clinician and the slide drawers 14, 16, 18, 20 are opened, the brackets 22, 24, 26, 28 are ready to be grasped with a suitable instrument, such as tweezers, and removed from the package 10 with a known orientation for immediate application to the patient's teeth. This minimizes the delays in providing a proper bracket orientation before bracket application. Brackets 22 held in slide drawer 14 are preferably oriented such that, for example, an archwire slot 22a of each bracket 22 is aligned with the archwire slot 22a of adjacent brackets 22. Similarly, brackets 24, 26, 28 held in slide drawers 16, 18, 20, respectively, are preferably oriented such that, for example, an archwire slot 24a, 26a, 28a of each of the brackets 24, 26, 28, respectively, is aligned with the archwire slot 24a, 26a, 28 of adjacent brackets 24, 26, 28. The archwire slots 22a, 24a, 26a, 28a may have other angular orientations (e.g., parallel alignment) so long as each has a substantially identical angular orientation. Other identifiable features, such as a tiewing or a bracket side edge, may be used as a guide for providing the common bracket angular orientation in each of the slide drawers 14, 16, 18, 20.

With reference to FIG. 3 and FIGS. 4A-D, the slide drawers 14, 16, 18, 20 of the package 10 are engaged with a cover 54 of the holder 12. The slide drawers 14, 16, 18, 20 are retained in engagement with the cover 54 by a retaining force sufficient to prevent inadvertent sliding movement by a manual force applied to the release tabs 30, 32, 34, 36. However, the engagement between the slide drawers 14, 16, 18, 20 is designed such that an intentionally applied manual force can overcome the retaining force for removing the slide drawers 14, 16, 18, 20 from the cover 54.

An upper face 55 of the cover 54 faces outwardly and contains printing and graphics, such as indicia 57 of the quadrant (UR/UL/LR/LL) of the patient's teeth that correspond to the respective slide drawers 14, 16, 18, 20 and any other product identification information. The printing and graphics, including indicia 57, may be provided on a separate label that is adhesively bonded to the upper face 55, or printed directly on the cover 54. A lower face 56 of the cover 54 faces toward or confronts the recesses 46, 48, 50, 52 defined in the inserts 38, 40, 42, 44.

Projecting from the lower face 56 of the cover 54 adjacent to the top and bottom sides 35, 37 are side walls 58, 60, respectively. Side wall 58 includes an inwardly-directed and longitudinally-extending flange 62 and another shorter inwardly-directed and longitudinally-extending flange 64 that is positioned between the lower face 56 of cover 54 and flange 62. Similarly, side wall 60 includes an inwardly-directed and longitudinally-extending flange 66 and another shorter inwardly-directed and longitudinally-extending flange 68 that is positioned between the lower face 56 of cover 54 and flange 66. A dividing wall or partition 70 projects from the lower face 56 of the cover 54 at a location approximately midway between the side walls 58, 60. A pair of longitudinally-extending flanges 72, 74 project laterally in opposition from the lower end of partition 70 and another pair of shorter longitudinally-extending flanges 76, 78 project laterally in opposition from partition 70 between the lower face 56 of cover 54 and flanges 72, 74, respectively.

Projecting from the lower face 56 of cover 54 at a position approximately midway between the side wall 58 and partition 70 is a dividing wall or partition 80. A pair of longitudinally-extending flanges 82, 84 project laterally in opposition from the lower end of partition 80. Similarly, projecting from the lower face 56 of cover 54 at a position approximately midway between the side wall 60 and partition 70 is a dividing wall or partition 86. A pair of longitudinally-extending flanges 88, 90 project laterally in opposition from the lower end of partition 80.

In the closed position, slide drawer 14 occupies a longitudinal channel 91 defined laterally between side wall 58 and partition 80. Similarly, slide drawer 16 occupies a longitudinal channel 92 defined laterally between partitions 80 and 70, slide drawer 18 occupies a longitudinal channel 93 defined laterally between partitions 70 and 86, and slide drawer 20 occupies a longitudinal channel 94 defined laterally between side wall 58 and partition 80. Each of the channels 91, 92, 93, 94 extends substantially the full distance between ends 31, 33 of cover 54.

With continued reference to FIG. 3 and FIGS. 4A-D, the slide drawers 14, 16, 18, 20 are coupled with the cover 54 by the flange structure of the side walls 58, 60 and partitions 70, 80, 86. To that end, opposed longitudinal side edge portions 14a, 14b of slide drawer 14 are positioned in the respective spaces defined between the bottom face 56 of cover 54 and flanges 64 and 82, which are confronting, approximately equal in length, and generally coplanar. Opposed longitudinal side edge portions 18a, 18b of slide drawer 18 are positioned in the respective spaces defined between the bottom face 56 of cover 54 and flanges 76 and 84, which are also confronting and generally coplanar. Opposed longitudinal side edge portions 16a, 16b of slide drawer 16 are positioned in the respective spaces defined between the bottom face 56 of cover 54 and flanges 78 and 90, which are also confronting and generally coplanar. Opposed longitudinal side edge portions 20a, 20b of slide drawer 20 are positioned in the respective spaces defined between the bottom face 56 of cover 54 and flanges 68 and 88, which are also confronting and generally coplanar.

Flange 62 has a contacting and supporting relationship with a bottom surface of the U-shaped slide drawer 14 when drawer 14 is at least partially engaged with the cover 54. Similarly, flange 66 has a contacting and supporting relationship with slide drawer 20 when drawer 20 is at least partially engaged with the cover 54. Flanges 72, 74 have a similar contacting and supporting relationship with the slide drawers 16, 18 when drawers 16, 18 are at least partially engaged with the cover 54. As a result, the manufacturing tolerances for the location of flanges 64, 68, 76, 78 relative to the lower face 56 of cover 54 may be relaxed. However, the contact between flange 62 and slide drawer 14, flange 66 and slide drawer 20, flange 72 and slide drawer 18, and flange 74 and slide drawer 16 provides a friction fit adequate to keep the slide drawers 14, 16, 18, 20 stationary and coupled with cover 54 against unintentional forces experienced during, for example, shipment from the supplier to the end user. However, the friction fit is loose enough that the slide drawers 14, 16, 18, 20 may be easily removed by a force applied to the respective release tabs 30, 32, 34, 36 by the clinician or clinician's assistant.

With reference to FIGS. 4A-4D in which like reference numerals refer to like features in FIGS. 1-3, the material forming each of the slide drawers 14, 16, 18, 20 is colored with a pigment or, alternatively, coated with a colored coating. The color of each of the slide drawers 14, 16, 18, 20 may be different so that they are perceived by the human eye as distinguishable based solely upon their coloration. This would permit each of the slide drawers 14, 16, 18, 20 to be color-coded for ready association with one quadrant of the patient's teeth. The slide drawers 14, 16, 18, 20 may be colored over their entire exposed surface area or only a portion of their surface area, such as, for example, the release tabs 30, 32, 34, 36 may be the only portions of slide drawers 14, 16, 18, 20 having the differential coloration suitable for distinguishing among the different slide drawers 14, 16, 18, 20. Those skilled in the art will appreciate that many potential variations for color-coding the slide drawers 14, 16, 18, 20 are possible to provide a visually identifiable color-coded indication of the intended quadrant of the patient's teeth for the corresponding set of brackets 22, 24, 26, 28.

Alternatively, a pair of the drawers, for example, drawers 14 and 16, may have one color and the other two of the drawers, for example, drawers 18 and 20, may have a different color of sufficient contrast to be distinguishable from drawers 14 and 16. This would permit one pair of drawers 14, 16 to be associated with the patient's upper arch and the other pair of drawers 18, 20 to be associated with the patient's lower arch. Alternatively, the single package 10 may include only two drawers in which one drawer is designated to hold orthodontic brackets for mounting to teeth in both quadrants of a patient's lower arch and the other drawer is designated to hold orthodontic brackets for mounting to teeth in both quadrants of a patient's upper arch.

The brackets 22 frictionally held in slide drawer 14 by the openings 46 in insert 38 include an optional marking 96 that may have the same color as slide drawer 14, as shown in FIG. 4A. The brackets 24 frictionally held in slide drawer 16 by the openings 48 in insert 40 include an optional orientation marking 98 on a tiewing that preferably has the same color as slide drawer 16. The brackets 26 frictionally held in slide drawer 18 by the openings 50 in insert 42 include an optional marking 100 on a tiewing that may have the same color as slide drawer 18. The brackets 28 frictionally held in slide drawer 20 by the openings 52 in insert 44 include an optional marking 102 on a tiewing that may have the same color as slide drawer 20. Preferably, the markings 96, 98, 100, 102 are color-coded with the slide drawers 14, 16, 18, 20, although the invention is not so limited as the markings 96, 98, 100, 102 on the brackets 22, 24, 26, 28 may be color coded with the setup card 104 (FIGS. 5A, 5B) as described below. To ensure proper placement, the colors of the markings 96, 98, 100, 102 are distinguishable from each other. Alternatively, other types of markings may be provided, such as distinct symbols and geometrical shapes, or the brackets 22, 24, 26, 28 may be constructed from materials of contrasting colors. Those skilled in the art will appreciate that many different configurations of markings 96, 98, 100, 102 on the brackets 22, 24, 26, 28 are possible to provide a visually identifiable color-coded indication of the intended quadrant of the patient's teeth.

Figure 5A:
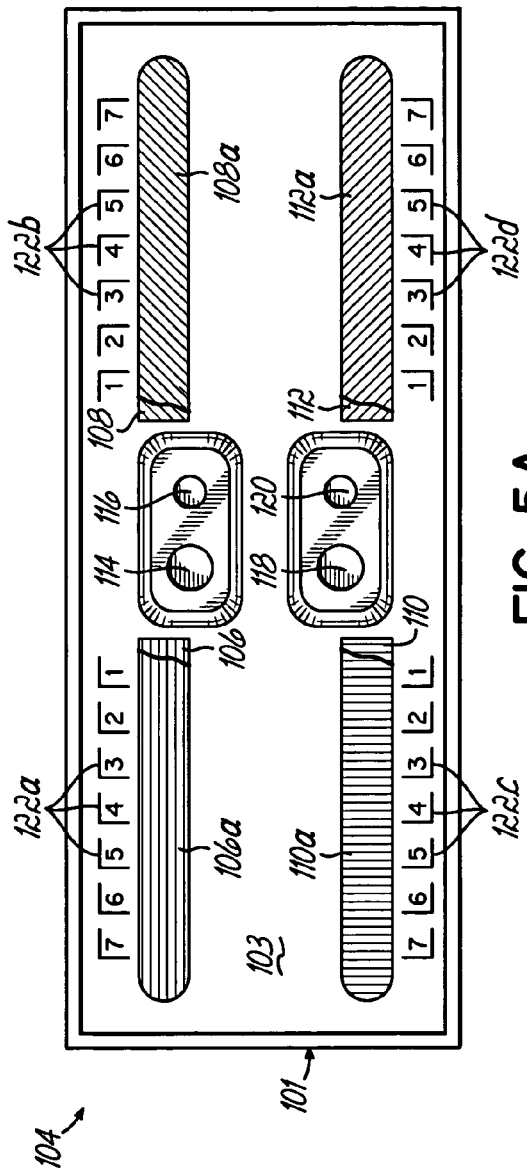
FIGS. 5A and 5B are top views of a setup card for use with the single patient bracket package of the invention.
Figure 5B:
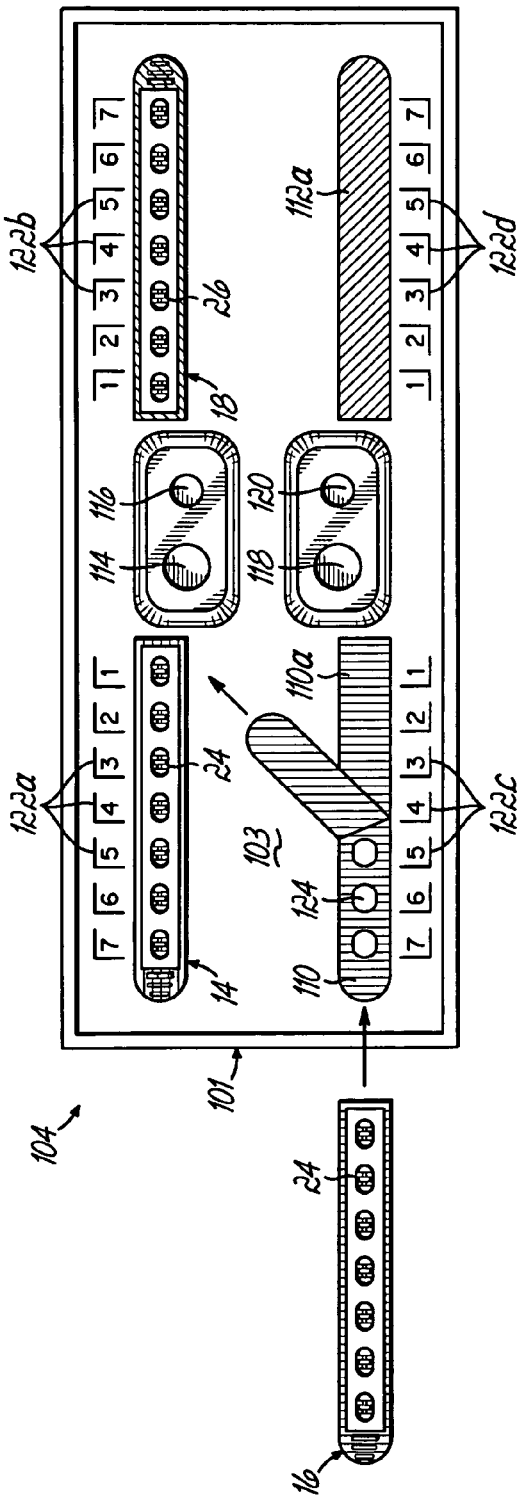

With reference to FIGS. 5A and 5B, a setup card 104 for use with the single patient bracket package 10 includes a substantially rigid, planar substrate 101 with an upper face 103 bearing multiple adhesive-coated colored strips 106, 108, 110, 112 each of which is covered by one of a plurality of flexible removable film layers 106a, 108a, 110a, 112a. Substrate 101 may be made of a suitable cardboard, a high-density polyethylene, a polystyrene, or any other suitable material, and of a suitable thickness to provide the desired rigidity. The setup card 104 includes four hollow circular bowl-shaped cavities 114, 116, 118, 120 that may be pre-filled by the supplier of the package 10 or may be provided empty to be filled by the clinician or the clinician's assistant with amount of chemicals, such as sealer/primer, adhesive, etc.

The colored strips 106, 108, 110, 112 and the removable film layers 106a, 108a, 110a, 112a are matched or coordinated in color. Furthermore, each of the colored strips 106, 108, 110, 112 and the respective overlying removable film layer 106a, 108a, 110a, 112a is matched or coordinated in color with one of the slide drawers 14, 16, 18, 20. This color coordination furnishes a color coding that assists the clinician or clinician's assistant in placing the slide drawers 14, 16, 18, 20 at proper locations on the setup card 104. The color coordination may be provided by identical colors, colors that are of slightly different hues, or any other systematic color-based matching system suitable to provide color coding. Those skilled in the art will appreciate that many different configurations of color-coding for colored strips 106, 108, 110, 112 and the removable film layers 106a, 108a, 110a, 112a are possible to provide a visually identifiable color-coded indication of the intended quadrant of the patient's teeth, in coordination with the color coding of the slide drawers 14, 16, 18, 20.

The upper face 103 of the setup card 104 faces upwardly when positioned on a tray or table, as might be present as a supporting surface adjacent to a dental chair in an orthodontist's office. The upper face 103 of setup card 104 may contain printing and graphics systematically indicating the specific tooth in each quadrant for bracket application. One approach is to identify the specific tooth with a unique label, such an identifier associated with the position of the corresponding tooth relative to the jaw centerline. One such system is to mark the location of the central incisor of the upper right quadrant with "1", mark the location of the lateral incisor with "2", mark the location of the cuspid with "3", mark the location of the first bicuspid with "4", mark the location of the second bicuspid with "5", mark the location of the first molar with "6", and mark the location of the second molar with "7". Indicia 122a, 122b, 122c, 122d of this style is provided on the setup card 104 for indicating the specific teeth of the upper right, upper left, lower right and lower left quadrants, respectively, associated with each of the brackets 22, 24, 26, 28 in slide drawers 14, 16, 18, 20.

A coating of a translucent or transparent pressure-sensitive adhesive is disposed between each of the colored strips 106, 108, 110, 112 and the corresponding removable film layer 106a, 108a, 110a, 112a. When the film layers 106a, 108a, 110a, 112a are peeled away to reveal the colored strips 106, 108, 110, 112, the adhesive coating remains fixed to the colored strips 106, 108, 110, 112 without significant loss of cohesion. After the film layers 106a, 108a, 110a, 112a are removed, the adhesive coating is effective to adhesively bond the drawers 14, 16, 18, 20 to the corresponding colored strips 106, 108, 110, 112 without loss of adhesion when the brackets 22, 24, 26, 28 are removed. The adhesive preferably extends in a continuous strip or bead centrally along the longitudinal axis of each colored strip 106, 108, 110, 112, although an interrupted strip or bead, a series of dots, or other pattern is also possible.

In an alternative embodiment of the invention, the individual brackets 22, 24, 26, 28 may be removed from the slide drawers 14, 16, 18, 20 and positioned directly on the setup card 104. To that end, each of the colored strips 106, 108, 110, 112 includes oval landing areas 124, visible in FIG. 5B for colored strip 110, that designate sites where the orthodontic brackets 22, 24, 26, 28 may be positioned or mounted. The landing areas 124 are of a different color than the respective colored strip 106, 108, 110, 112 so as to clearly mark the site for bracket positioning. One of the landing areas 124 on each of the colored strips 106, 108, 110, 112 corresponds to each of the indicia 122a, 122b, 122c, 122d, which assists the clinician or clinician's assistant in properly positioning the brackets 22, 24, 26, 28 on the appropriate landing areas 124. The adhesive coating on each of the colored strips 106, 108, 110, 112 is present across the landing areas 124 and should be effective for adhesively securing the respective brackets 22, 24, 26, 28 to preserve their positions until application without significant adhesive transfer upon removal.

In another alternative embodiment of the invention, the slide drawers 14, 16, 18, 20 may be of a uniform color and, instead, the markings 96, 98, 100, 102 (FIGS. 4A-D) may be color-coded with the colored strips 106, 108, 110, 112 and the corresponding removable film layer 106a, 108a, 110a, 112a of setup card 104. In this embodiment, the clinician or clinician's assistant would match the markings 96, 98, 100, 102 with the colored strips 106, 108, 110, 112 and removable film layers 106a, 108a, 110a, 112a when transferring the drawers 14, 16, 18, 20 or the individual brackets 22, 24, 26, 28 from the single patient bracket package 10 to the setup card 104.

In use and with reference to FIGS. 1-5, the slide drawers 14, 16, 18, 20 of the single patient bracket package 10 are filled with oriented orthodontic brackets 22, 24, 26, 28 and shipped to the end user clinician. During shipment, the orientation of the orthodontic brackets 22, 24, 26, 28 is maintained by the resiliency of the material of the insert 38, 40, 42, 44 surrounding the recesses 46, 48, 50, 52. At the clinician's office, the single patient bracket package 10 is placed on a table or tray adjacent a dental chair in an orthodontist's office. The clinician or clinician's assistant moves each of slide drawers 14, 16, 18, 20 to an opened position by manipulating the corresponding release tabs 30, 32, 34, 36, preferably with a gloved hand.

The slide drawers 14, 16, 18, 20 removed from the holder 12 are transferred to the setup card 104 and positioned on one of the colored strips 106, 108, 110, 112, according to the color coding. The corresponding color-coded removable layers 106a, 108a, 110a, 112a are preferably peeled away to reveal the adhesive coating on the colored strips 106, 108, 110, 112 so that the slide drawers 14, 16, 18, 20 are adhesively bonded with the setup card 104. Advantageously, indicia 122a, 122b, 122c, 122d printed on the upper face 103 of setup card 104 are correlated with the corresponding bracket locations in each drawer 14, 16, 18, 20 and placed on the setup card 104 so that the proper bracket 22, 24, 26, 28 can be quickly selected at all times and mounted to the appropriate tooth in the appropriate quadrant.

As shown in FIG. 5B, the slide drawers 14, 16 bearing orthodontic brackets 22, 24, respectively, for the upper right quadrant and upper left quadrant of the patient have already been applied to the colored strips 106, 108 of the setup card 104, with the film layer 110a of the colored strip 110 being removed to expose the adhesive for the slide drawer 16 bearing orthodontic brackets 24 for the lower right quadrant of the patient. Alternatively, the individual orthodontic brackets 22, 24, 26, 28 may be transferred from the slide drawers 14, 16, 18, 20 to the landing areas 124 on the setup card 104.

After the setup card 104 is populated at chairside with the orthodontic brackets 22, 24, 26, 28, each bracket 22, 24, 26, 28 is individually grasped with a suitable hand instrument, such as tweezers, lifted in a direction away from the setup card 104, and mounted to a tooth in a corresponding quadrant of the patient's teeth after an adhesive, such as a light cure or UV adhesive, is applied to the bracket's bond pad. The adhesive is cured by exposure to radiation from a suitable curing light to bond each bracket 22, 24, 26, 28 to the corresponding tooth. Any unused orthodontic brackets 22, 24, 26, 28 that are not applied to the patient's teeth may be conveniently stored by the clinician in the single patient package 10 by removing the drawers 14, 16, 18, 20 from the setup card 104 and reinserting them into the holder 12.

Alternatively, the setup card 104 including the adhesively bonded drawers 14, 16, 18, 20 and holder 12 may be discarded.

In an alternative embodiment, the brackets 22, 24, 26, 28 may be applied to the patient's teeth directly from the slide drawers 14, 16, 18, 20 without using the setup card 104. To that end, each of the drawers 14, 16, 18, 20 is pulled only partially from the holder 12 so that each is retained and supported within the respective one of channels 91, 92, 93, 94. Each bracket 22, 24, 26, 28 is grasped with a suitable hand instrument, such as tweezers, lifted in a direction away from the respective drawer 14, 16, 18, 20, and mounted to a tooth in a corresponding quadrant of the patient's teeth after an adhesive, such as a light cure or UV adhesive, is applied to the bracket's bond pad. The adhesive is cured by exposure to radiation from a suitable curing light to provide a bond. Any unused orthodontic brackets 22, 24, 26, 28 that are not applied to the patient's teeth may be conveniently stored by the clinician in the single patient package 10.

Figure 6:
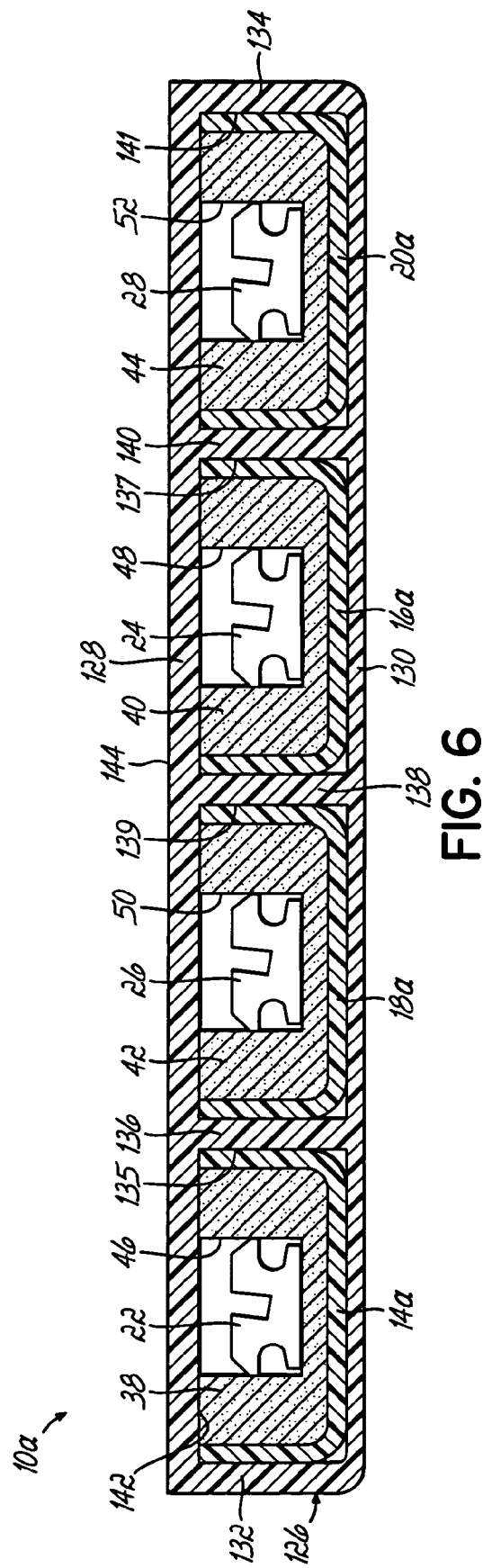
FIG. 6 is a cross-sectional view similar to FIG. 3 showing an alternative embodiment of the single patient package of the invention.

With reference to FIG. 6 in which like reference numerals refer to like features in FIGS. 1-3 and in accordance with an alternative embodiment of the invention, a single patient package 10a includes slide drawers 14a, 16a, 18a, 20a holding orthodontic brackets 22, 24, 26, 28, respectively. Slide drawers 14a, 16a, 18a, 20a have color-coding identical similar that described above for slide drawers 14, 16, 18, 20 (FIGS. 4A-D).

Package 10a includes a holder 126 having upper and lower covers 128, 130 joined at their side edges by side walls 132, 134 defining the lateral boundaries of the holder 126. Extending between the upper and lower covers 128, 130 is a plurality of dividing walls or partitions 136, 138, 140 that operate to divide the space defined laterally between the side walls 132, 134 and vertically between upper and lower covers 128, 130 into a plurality of four channels 135, 137, 139, 141 each slidably supporting one of the slide drawers 14a, 16a, 18a, 20a. The slide drawers 14a, 16a, 18a, 20a are oriented such that the respective recesses 46, 48, 50, 52 in inserts 38, 40, 42, 44, respectively, open toward a lower face 142 of the upper cover 128. The slide drawers 14a, 16a, 18a, 20a are held stationary within the channels 135, 137, 139, 141 until intentionally removed from the holder 126 for mounting to different quadrants of a patient's teeth. An upper face 144 of upper the cover 128 faces outwardly and contains printing and graphics similar to indicia 57 of cover 54 (FIG. 3).

References herein to terms such as "vertical", "horizontal", "on", "above", "below", "side" (as in "side wall"), "lower", "over", "beneath", "under" etc. are made by way of example, and not by way of limitation, to establish a frame of reference. It is understood that various other frames of reference may be employed without departing from the spirit and scope of the invention.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A kit for use in orthodontic treatment of a patient's teeth, comprising:
   a holder including a plurality of drawers that are removable from said holder;
   a plurality of dental appliances received in said drawers; and
   a setup card having a plurality of regions defining respective placement locations for receiving said drawers,
   wherein each of said regions on said setup card and a corresponding one of said drawers include one of a plurality of different colors, and said dental appliances in each of said drawers are configured for use in one quadrant of the patient's teeth.

2. The kit of claim 1 wherein each of said drawers has a plurality of recesses defined therein for receiving said dental appliances.

3. The kit of claim 2 wherein each of said dental appliances includes an indicia correlated with one of said different colors.

4. The kit of claim 1 wherein each of said regions includes a plurality of landing zones for receiving the dental appliances, each landing zone having a color that contrasts with said color of said region.

5. The kit of claim 1 wherein each of said regions includes an adhesive for securing each of said drawers to a corresponding one of said regions.

6. The kit of claim 5 wherein said setup card further includes a plurality of color-coded removable layers each adhered removably with one of said regions, and each of said removable layers includes one of said different colors.

7. A method for using a package with multiple drawers each holding dental appliances intended for use in a different quadrant of a patient's teeth, comprising:
   opening a first drawer to access the dental appliances intended for use only on a first quadrant of the patient's teeth;
   separating the first drawer from the package;
   placing the first drawer on a setup card;
   removing the dental appliances from the first drawer; and
   mounting the dental appliances removed from the first drawer to the patient's teeth in the first quadrant.

8. The method of claim 7 wherein placing the first drawer on the setup card further comprises:
   adhesively securing the first drawer to the setup card.

9. The method of claim 7 wherein the setup card includes a plurality of strips having different colors, the first drawer having a color that corresponds with one of the different colors, and placing the first drawer on the setup card further comprises:
   positioning the first drawer on the one of the strips having the corresponding color.

10. The method of claim 9 wherein each of the dental appliances in the first drawer includes an indicia with the color of the first drawer.

11. A method for using a package with multiple drawers each holding dental appliances intended for use in a different quadrant of a patient's teeth, comprising:
    opening a first drawer to access the dental appliances intended for use only on a first quadrant of the patient's teeth;
    separating the first drawer from the package;
    transferring each of the dental appliances from the first drawer to one of a plurality of landing zones on a setup card; and
    mounting the dental appliances removed from the first drawer to the patient's teeth in the first quadrant.

12. A method for bonding dental appliances to a patient's teeth, comprising:
selecting from a package a first drawer containing dental appliances intended for use on a first quadrant of the patient's teeth;
placing the first drawer on a setup card having adhesive thereon for holding the first drawer in place;
selecting dental appliances from the first drawer; and
mounting the dental appliances to the patient's teeth in the first quadrant.

13. The method of claim 12 further comprising:
selecting from the package a second drawer containing dental appliances intended for use on a second quadrant of the patient's teeth;
placing the second drawer on the setup card having adhesive thereon for holding the second drawer in place;
selecting dental appliances from the second drawer; and
mounting the dental appliances to the patient's teeth in the second quadrant.

14. The method of claim 12 wherein the first and second drawers are removed from opposite ends of the package.

15. The method of claim 12 wherein the setup card includes a plurality of adhesively-covered strips having different colors, the first drawer having a first color that corresponds with one of the different colors, and placing the first drawer on the setup card further comprises:
positioning the first drawer on the one of the strips having the first color.

16. The method of claim 15 wherein each of the dental appliances in the first drawer includes an indicia with the first color.

17. The method of claim 12 wherein removing the first drawer comprises:
sliding the first drawer along a channel defined in the package.

18. The method of claim 12 wherein the first drawer has a longitudinal axis and each of the dental appliances in the first drawer has a feature, and further comprising:
orienting the feature of each of the dental appliances with a common angular orientation relative to the longitudinal axis of the first drawer.

19. A method for using a package holding multiple drawers each having a different color, each of the drawers containing dental appliances intended for use in a different quadrant of a patient's teeth, comprising:
removing from the package a first drawer having a first color and containing dental appliances for use on a first quadrant of the patient's teeth;
positioning the first drawer on a first region of a setup card having the first color;
removing the dental appliances from the first drawer; and
mounting the dental appliances removed from the first drawer on the patient's teeth in the first quadrant.

20. The method of claim 19 wherein positioning the first drawer on the region further comprises:
adhesively coupling the first drawer with the first region.

21. The method of claim 19 further comprising:
selecting from the package a second drawer having a second color and containing dental appliances for use on a second quadrant of the patient's teeth;
placing the second drawer on a second region of the setup card having the second color;
removing the dental appliances from the second drawer; and
mounting the dental appliances to the patient's teeth in the second quadrant.

22. The method of claim 21 wherein the first and second drawers are removed from opposite ends of the package.

23. The method of claim 19 wherein each of the dental appliances in the first drawer includes an indicia with the first color.

24. The method of claim 19 wherein removing the first drawer comprises:
sliding the first drawer along a channel defined in the holder.

25. The method of claim 19 wherein the first drawer has a longitudinal axis and each of the dental appliances in the first drawer has a feature, and further comprising:
orienting the feature of each of the dental appliances with a common angular orientation relative to the longitudinal axis of the first drawer.

26. A method for using a package holding multiple drawers each containing dental appliances with an indicia of a different color and intended for use in a different quadrant of a patient's teeth, comprising:
removing from the package a first drawer containing dental appliances having an indicia with a first color and configured for use on a first quadrant of the patient's teeth;
positioning the first drawer on a first region of a setup card having a first color corresponding to the first colored indicia;
removing the dental appliances from the first drawer; and
mounting the dental appliances removed from the first drawer on the patient's teeth in the first quadrant.

27. The method of claim 26 wherein positioning the first drawer on the region further comprises:
adhesively coupling the first drawer with the first region.

28. The method of claim 26 further comprising:
selecting from the package a second drawer containing dental appliances with an indicia of a second color for use on a second quadrant of the patient's teeth;
placing the second drawer on a region of the setup card having a corresponding second color corresponding to the second colored indicia;
selecting dental appliances from the second drawer; and
mounting the dental appliances to the patient's teeth in the second quadrant.

29. The method of claim 28 wherein the first and second drawers are removed from opposite ends of the package.

30. The method of claim 26 wherein removing the first drawer comprises:
sliding the first drawer along a channel defined in the holder.

31. The method of claim 26 wherein the first drawer has a longitudinal axis and each of the dental appliances in the first drawer has a feature, and further comprising:
orienting the feature of each of the dental appliances with a common angular orientation relative to the longitudinal axis of the first drawer.

* * * * *

UNITED STATES PATENT AND TRADEMARK OFFICE
CERTIFICATE OF CORRECTION

PATENT NO. : 7,338,282 B2  
APPLICATION NO. : 10/940318  
DATED : March 4, 2008  
INVENTOR(S) : Kevin Sean Corcoran Page 1 of 1

It is certified that error appears in the above-identified patent and that said Letters Patent is hereby corrected as shown below:

Column 6, line 12, change "28" to --28a--.

Column 11:  
Line 26-27, change "identical similar" to --identical or similar to--.  
Line 46, change "upper the" to --the upper--.

Signed and Sealed this

Third Day of March, 2009

JOHN DOLL  
*Acting Director of the United States Patent and Trademark Office*